United States Patent [19]

Goldhaber et al.

[11] Patent Number: 5,269,946
[45] Date of Patent: Dec. 14, 1993

[54] SYSTEMS AND METHODS FOR REMOVING UNDESIRED MATTER FROM BLOOD CELLS

[75] Inventors: Richard Goldhaber, Lake Forest; Daniel F. Bischof, McHenry, both of Ill.

[73] Assignee: Baxter Healthcare Corporation, Deerfield, Mich.

[21] Appl. No.: 704,063

[22] Filed: May 22, 1991

[51] Int. Cl.⁵ .............................................. B01D 37/00
[52] U.S. Cl. ...................... 210/767; 210/257.1; 604/406; 604/410; 422/41; 422/44
[58] Field of Search ............ 210/767, 749, 806, 787, 210/196, 233, 257.1, 500.42; 604/406, 408, 410; 422/41, 44; 435/2

[56] References Cited

U.S. PATENT DOCUMENTS

| | | | |
|---|---|---|---|
| 4,267,269 | 5/1981 | Grode et al. | 435/2 |
| 4,915,848 | 4/1990 | Carmen et al. | 210/749 |
| 4,919,823 | 4/1990 | Wisdom | 210/749 |
| 4,943,287 | 7/1990 | Carmen | 604/408 |
| 4,977,527 | 3/1991 | Stewart | 210/767 |
| 4,985,153 | 1/1991 | Kuroda et al. | 210/782 |
| 5,089,146 | 2/1992 | Carmen et al. | 210/782 |
| 5,104,788 | 4/1992 | Carmen et al. | 435/2 |

Primary Examiner—Robert A. Dawson
Assistant Examiner—Sun Uk Kim
Attorney, Agent, or Firm—Paul C. Flattery; Bradford R. L. Price; Daniel D. Ryan

[57] ABSTRACT

Systems and methods of collecting blood cells use a first container connected to at least three transfer containers. A filtration system is provided with one transfer container, which ultimately serves as the storage container for red blood cells free of white blood cells. The two other transfer containers are connected to each other, one of which is empty and one of which contains and additive solution for storage of red blood cells. The empty transfer container is used for storage of platelet concentrate, while the container that originally contained the additive solution is ultimately used to store the platelet-poor plasma component. A portion of the additive solution may be separately passed through the filtration system after filtration of the red cells to flush additional red blood cells from the filtration device.

19 Claims, 4 Drawing Sheets

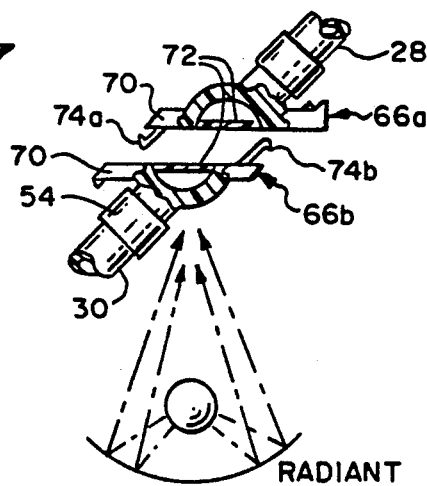
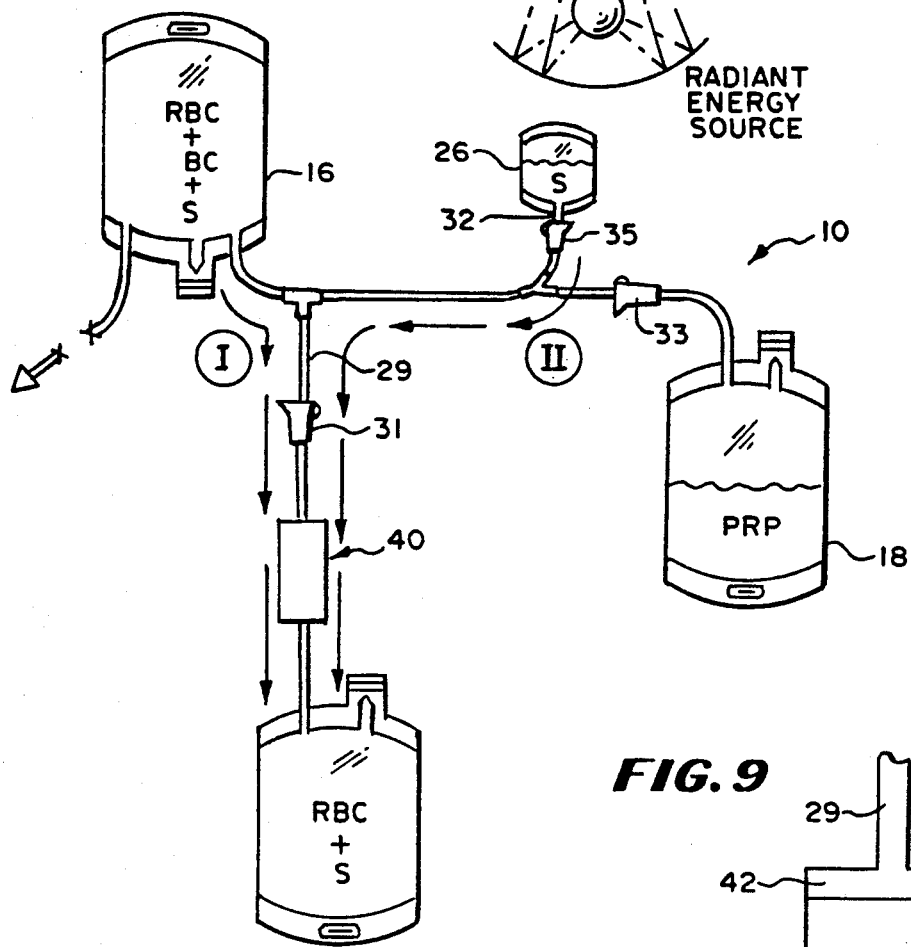
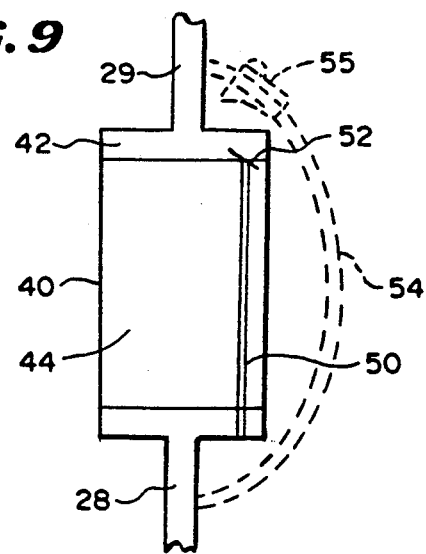

5,269,946

SYSTEMS AND METHODS FOR REMOVING UNDESIRED MATTER FROM BLOOD CELLS

FIELD OF THE INVENTION

The invention generally relates to blood collection and processing systems and methods. In a more particular sense, the invention relates to systems and methods for removing white blood cells from red blood cells prior to transfusion or long term storage.

BACKGROUND OF THE INVENTION

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Systems composed of multiple, interconnected plastic bags have met widespread use and acceptance in the collection, processing and storage of these blood components. In the United States, these multiple blood bag systems are subject to regulation by the government. For example, the plastic materials from which the bags and tubing are made must be approved by the government. In addition, the maximum storage periods for the blood components collected in these systems are prescribed by regulation.

In the United States, whole blood components collected in a nonsterile, or "open", system (i.e. one that is open to communication with the atmosphere) must, under governmental regulations, be transfused within twenty-four hours. However, when whole blood components are collected in a sterile, or "closed", system (i.e., one that is closed to communication with the atmosphere), the red blood cells can be stored up to forty-two days (depending upon the type of anticoagulant and storage medium used); the platelet concentrate can be stored up to five days (depending upon the type of storage container); and the platelet-poor plasma may be frozen and stored for even longer periods. Conventional systems of multiple, interconnected plastic bags have met with widespread acceptance, because these systems can reliably provide the desired sterile, "closed" environment for blood collection and processing, thereby assuring the maximum available storage periods.

In collecting whole blood components for transfusion, it is desirable to minimize the presence of impurities or other materials that may cause undesired side effects in the recipient. For example, because of possible febrile reactions, it is generally considered desirable to transfuse red blood cells substantially free of the white blood cell components, particularly for recipients who undergo frequent transfusions.

One way to remove white blood cells is by washing the red blood cells with saline. This technique is time consuming and inefficient, as it can reduce the number of red blood cells available for transfusion. The washing process also exposes the red blood cells to communication with the atmosphere, and thereby constitutes a "non-sterile" entry into the storage system. Once a non-sterile entry is made in a previously closed system, the system is considered "opened", and transfusion must occur within twenty-four hours, regardless of the manner in which the blood was collected and processed in the first place. In the United States, an entry into a blood collection system that presents the probability of non-sterility that exceeds one in a million is generally considered to constitute a "non-sterile" entry.

Another way to remove white blood cells is by filtration. Systems and methods for accomplishing this within the context of conventional multiple blood bag configurations are described in Wisdom U.S. Pat. Nos. 4,596,657 and 4,767,541, as well as in Carmen et al U.S. Pat. Nos. 4,810,378 and 4,855,063. In these arrangements, an inline white blood cell filtration device is used. The filtration can thereby be accomplished in a closed system. However, the filtration processes associated with these arrangements require the extra step of wetting the filtration device before use with a red blood cell additive solution or the like. This added step complicates the filtration process and increases the processing time.

Other systems and methods for removing white blood cells in the context of closed, multiple blood bag configurations are described in Stewart U.S. Pat. No. 4,997,577. In these filtration systems and methods, a transfer assembly dedicated solely to the removal of white blood cells is used. The transfer assembly is attached to a primary blood collection container. The transfer assembly has a transfer container and a first fluid path leading to the transfer container that includes an inline device for separating white blood cells from red blood cells. The transfer assembly also has a second fluid path that bypasses the separation device. Using these systems and methods, white blood cells are removed as the red blood cells are conveyed to the transfer container through the first fluid path. The red blood cells, now substantially free of white blood cells, are then conveyed from the transfer container back to the primary collection container for storage through the second fluid path, this time bypassing the separation device.

A need still exists for further improved systems and methods for removing undesired matter from blood components prior to transfusion or storage in a way that lends itself to use in closed multiple blood bag system environments.

SUMMARY OF THE INVENTION

The invention provides a multiple container blood collection system for conveniently processing the various components of blood. The system includes a device for separating the undesired matter during processing. The system is arranged so that some components can be conveyed through the separation device, while other components can be readily conveyed along other paths that bypass the separation device. The system is also arranged so that only a single pass through the separation device is required during a given processing sequence.

The invention provides a blood collection system that includes a blood collection assembly, a first transfer assembly, and a second transfer assembly. The first transfer assembly has an empty first transfer container and a second transfer container that contains an additive solution. The second transfer assembly has a third transfer container and a fluid path that leads to the third transfer container and that includes means for separating undesired matter from blood. The system also has flow control means operable in various processing modes for directing fluid flow within the system.

In one arrangement, the flow control means includes four processing modes. In a first mode, the flow control means directs a first quantity of blood from the blood collection assembly for collection in the first transfer container. In a second mode, the flow control means directs additive solution from the second transfer container into the blood collection assembly to mix with the quantity of blood remaining in the blood collection assembly. In a third mode, the flow control means directs the mixture of the additive solution and the remaining blood from the blood collection assembly to the third transfer container through the separation means to remove the undesired materials. In a fourth mode, the flow control means directs a constituent of the blood contained in the first transfer container into the second transfer container for collection.

In another arrangement, the flow control means includes five processing modes. In a first mode, the flow control means directs a first quantity of blood from the blood collection assembly for collection in the first transfer container. In a second mode, the flow control means directs a first quantity, but not all, of the additive solution from the second transfer container into the blood collection assembly to mix with the quantity of blood remaining in the blood collection assembly. In a third mode, the flow control means directs the mixture of the additive solution and the remaining blood from the blood collection assembly to the third transfer container through the separation means to remove the undesired materials. In a fourth mode, the flow control means directs the remaining quantity of the additive solution from the second transfer container into the third transfer container through the separation means, thereby using the remaining additive solution to flush the separation means as it is being conveyed to the third transfer container. In a fifth mode, the flow control means directs a constituent of the blood contained in the first transfer container into the second transfer container for collection.

In either embodiment, the second transfer assembly can include means for venting air from the third transfer container in a path that bypasses the separation means.

Also in either embodiment, at least one of the blood collection assembly, the first transfer assembly, and the second transfer assembly can comprise an initially separate subassembly. In this arrangement, the system further includes means for attaching the separate subassembly to the other parts of the system at time of use.

The invention also provides methods of collecting blood components substantially free of undesired matter using the systems as just generally described.

The invention provides blood processing systems and methods in which separation is accomplished using a minimum number of bags or other containers. Since the container that serves as the blood additive container prior to separation also serves as a storage container for one of the blood components after separation, economies are realized.

The systems and methods that embody the features of the invention are particularly well suited for use in association with closed blood collection systems and conventional sterile connection techniques, thereby permitting separation to occur in a sterile, closed environment.

While the systems and methods that embody the features of the invention can be used to process all types of blood components, they are well suited for the removal of white blood cells from red blood cells by filtration prior to transfusion or long term storage.

Other features and advantages of the invention will become apparent upon review of the following description, drawings, and appended claims.

BRIEF DESCRIPTION OF THE DRAWINGS

FIG. 7 is an enlarged side sectional view of the sterile connection devices associated with the systems shown in FIG. 6;

FIG. 8 is a schematic view of the system shown in FIG. 1 being used with an alternative step of flushing the separation device with a portion of the additive solution after filtration is completed; and FIG. 9 is broken away sectional view of a filtration device usable in association with the system shown in FIG. 1 and having an air bleed channel for venting air from the transfer container.

DESCRIPTION OF THE PREFERRED EMBODIMENT

Figure 1:
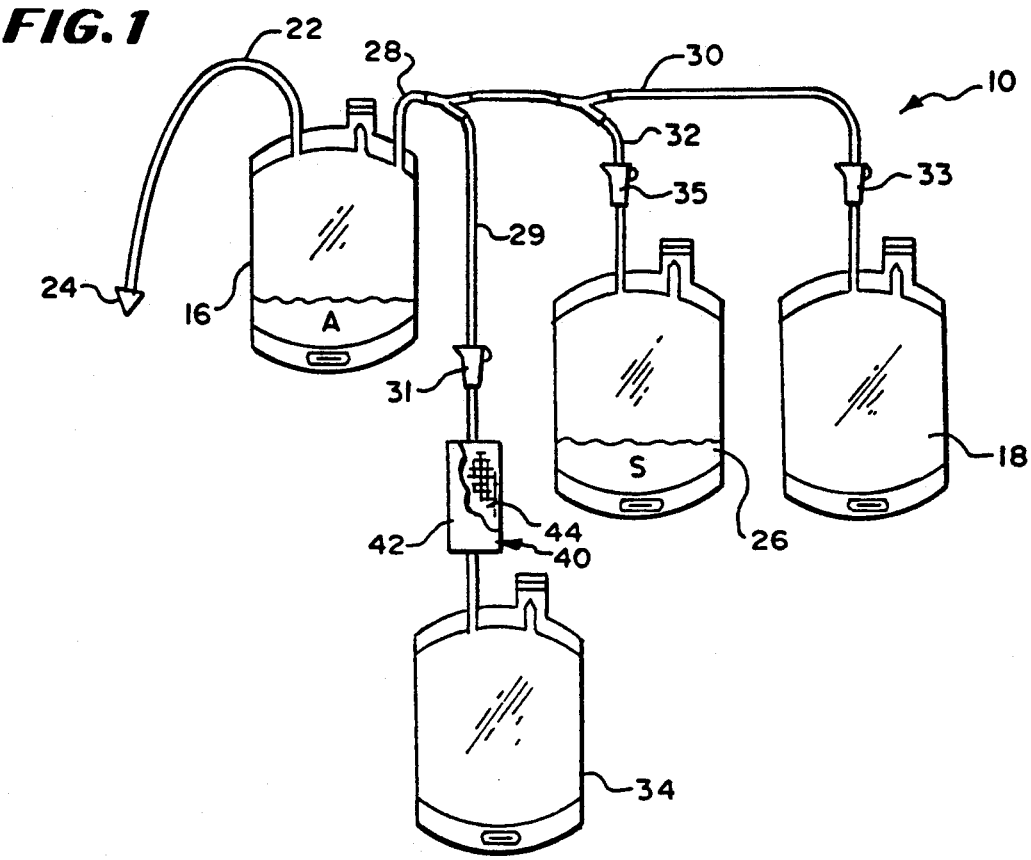
FIG. 1 is a schematic view of a blood collection system of the present invention.

A blood collection assembly 10 is shown in FIG. 1. The assembly 10 comprises a closed blood collection system. In the illustrated embodiment, the assembly 10 serves to separate and store the red blood cells as well as the plasma and platelet blood components by conventional centrifugation techniques, while removing undesired matter from the red blood cells prior to storage. In the illustrated embodiment, the undesired matter is removed by filtration.

As used herein, the term "filtration" is intended to include separation achieved by various centrifugal and non-centrifugal techniques, and not merely "filtration" in the technical sense. Separation can occur by absorption, columns, chemical, electrical, and electromagnetic means. The term "filtration" is thus broadly used in this specification to encompass all of these separation techniques as well.

In the illustrated and preferred embodiment shown in FIG. 1, the assembly 10 includes a primary bag or container 16 and various transfer bags or containers 18, 26, and 34 that are attached to the primary bag 16 by integrally attached branched tubing 28. The tubing 28 is divided by appropriate connectors into branches 29, 30, and 32.

In the illustrated embodiment, flow control devices 31, 33, and 35 are provide on the branched fluid flow paths as shown to enable directing of the fluid transfers in a desired sequence of steps. In the illustrated arrangement, the flow control devices take the form of conventional roller clamps that are manually operated to open and close the associated tubing paths.

In use, the primary bag 16 (which is also called a donor bag) receives whole blood from a donor through integrally attached donor tubing 22 that carries an phlebotomy needle 24. A suitable anticoagulant A is contained in the primary bag 16.

The transfer bag 26 contains a suitable storage solution S for the red blood cells. One such solution is disclosed in Grode et al U.S. Pat. No. 4,267,269.

The transfer bag 18 is intended to receive the platelet and plasma blood components associated with the whole blood collected in the primary bag 16. According to the invention, the transfer bag 18 ultimately serves as the storage container for the platelet concentrate constituent. Also according to the invention, the transfer bag 26 also ultimately serves as the storage container for the platelet-poor plasma constituent.

Flow control device 33 is located in tubing 30 to control fluid flow to and from the transfer bag 18. Flow control device 35 is located in tubing 32 to control fluid flow to and from transfer bag 26.

Tubing 28 and 29 form a flow path to the container 34. This flow path includes an inline filtration device 40 for separating undesired matter from blood cells. Flow control means 31 is located on tubing 29 which leads to a separation device 40. According to the invention, the container 34 ultimately serves as a storage container for the red blood cells after passage through the separation device 40.

The bags and tubing associated with the processing assembly 10 can be made from conventional approved medical grade plastic materials, such as polyvinyl chloride plasticized with di-2-ethylhexyl-phthalate (DEHP). The ends of the tubing may be connected by a "Y" or "T" connectors to form the branched fluid flow paths.

Alternatively, transfer container 18, which is intended to store the platelet concentrate, can be made of polyolefin material (as disclosed in Gajewski et al U.S. Pat. No. 4,140,162) or a polyvinyl chloride material plasticized with tri-2-ethylhexyl trimellitate (TEHTH). These materials, when compared to DEHP-plasticized polyvinyl chloride materials, have greater gas permeability that is beneficial for platelet storage.

The blood collection and storage assembly 10, once sterilized, constitutes a sterile, "closed" system, as judged by the applicable standards in the United States.

When the system 10 is used according to the invention, whole blood is collected in the primary bag 16. The collected whole blood is centrifugally separated within the primary bag 16 into a red blood cell component (designated RBC in FIG. 2) and platelet-rich plasma component (designated PRP in FIG. 2). During such separation techniques, a layer of white blood cells (commonly called the "buffy coat" and designated BC in FIG. 2) forms between the red blood cells and the platelet-rich plasma.

In a first processing mode (shown in FIG. 2), the platelet-rich plasma component is transferred by conventional techniques from the primary bag 16 to the transfer bag 18. This transfer is accomplished by opening clamp 33, while closing clamps 31 and 35. In this step, attempts are made to keep as many white blood cells in the primary bag 16 as possible. The transfer of platelet-rich plasma into the first transfer bag 18 leaves the red blood cells and the remaining white blood cells behind in the primary bag 16.

In a second processing mode (shown in FIG. 3), the solution S is transferred from the transfer bag 26 into the primary bag 16. This transfer is accomplished, by closing clamps 31 and 33, while opening clamp 35.

In a third processing mode (shown in FIG. 4), the mixture of additive solution S and the red blood and white blood cells in the primary bag 16 is transferred into the transfer bag 34 via the separation device 40. This transfer is accomplished by closing the clamps 33 and 35 while opening the clamp 31. The red blood cells and additive solution S enter the container 34 essentially free of white blood cells.

It should be appreciated that the filtration means 40 can be used to remove all types of undesired materials from different types blood cells, depending upon its particular construction. In the illustrated embodiment, the filtration device 40 is intended to remove white blood cells (and preferably also platelets) from the red blood cells prior to storage. In this arrangement, the filtration device 40 includes a housing 42 containing a conventional filtration medium 44 suited for the removal of white blood cells and platelets from red blood cells. The filtration medium 44 can include cotton wool, cellulose acetate or another synthetic fiber like polyester. The undesired matter (i.e., white blood cells and platelets) are removed from the red blood cells by the filtration device 40.

Figure 2:
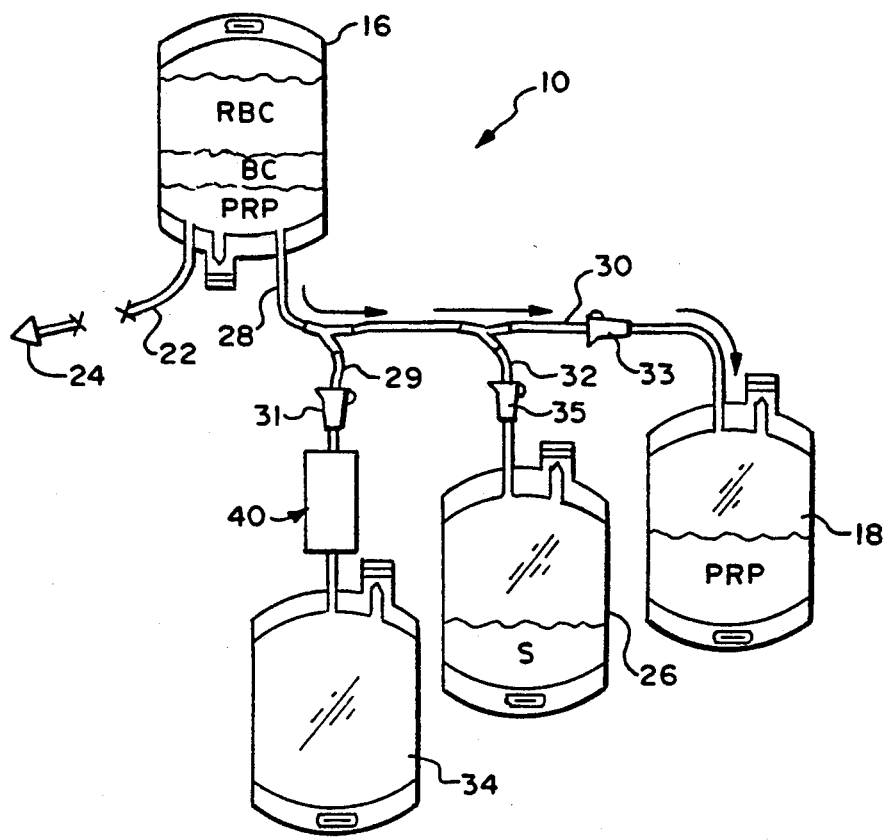
FIG. 2 is a schematic view of the system shown in FIG. 1 being used to transfer platelet-rich component to an associated transfer assembly.
Figure 4:
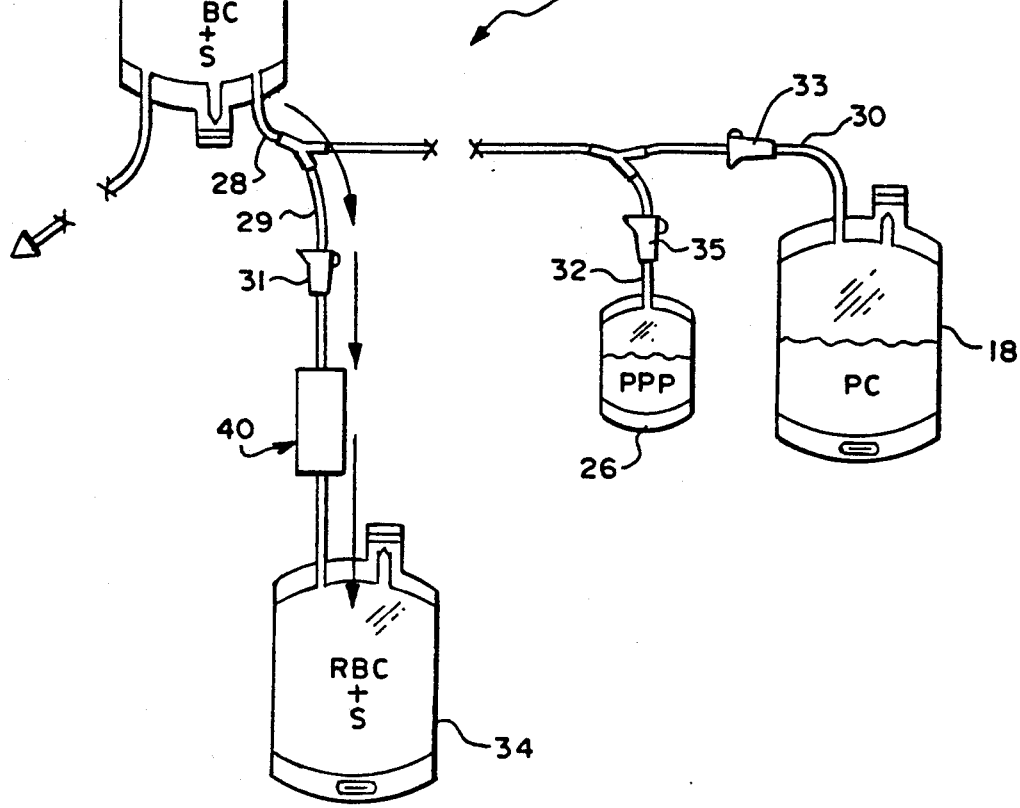
FIG. 4 is a schematic view of the system shown in FIG. 1 being used to remove undesired matter from the red blood cells in another transfer assembly, while platelet and plasma separation occurs in the now separated first transfer assembly.

In a fourth processing mode (shown in FIGS. 4 and 5), a constituent of the component contained in the transfer bag 18 is transferred to the transfer bag 26. In the illustrated embodiment, this processing mode is accomplished by first separating the transfer bags 18 and 26 from the system 10 (as FIG. 4 shows). The separation of the bags is accomplished by forming snap-apart seals in the tubing 30 that makes up the branched fluid flow path 30 leading to the transfer bags 18 and 26. A conventional heat sealing device (for example, the Hematron ® dielectric sealer sold by Baxter Healthcare Corporation) can be used for this purpose. This device forms a hermetic, snap-apart seal in the tubing 30 (this seal is schematically shown by an "x" in FIGS. 4 and 5). Preferably, the donor tubing 22 is also sealed and disconnected in the same fashion (as shown in FIG. 2).

Figure 5:
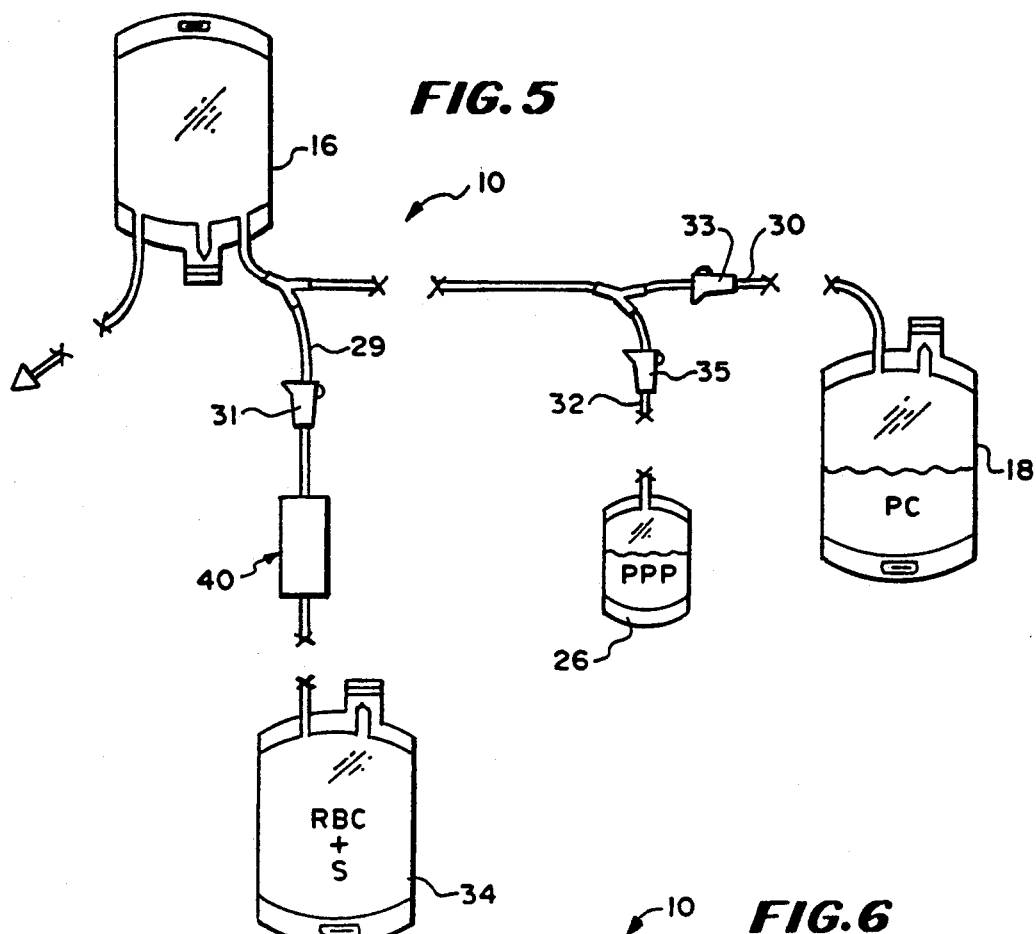
FIG. 5 is a schematic view of the system shown in FIG. 1 with all the associated storage containers separated for the storage of individual components.

Once separated, the platelet-rich plasma undergoes subsequent centrifugal separation within the transfer bag 18 into platelet concentrate (designated PC in FIGS. 4 and 5) and platelet-poor plasma (designated PRP in FIGS. 4 and 5). The platelet-poor plasma is transferred into the transfer bag 26 (by opening the clamps 33 and 35), leaving the platelet concentrate in the first transfer bag 18.

Figure 3:
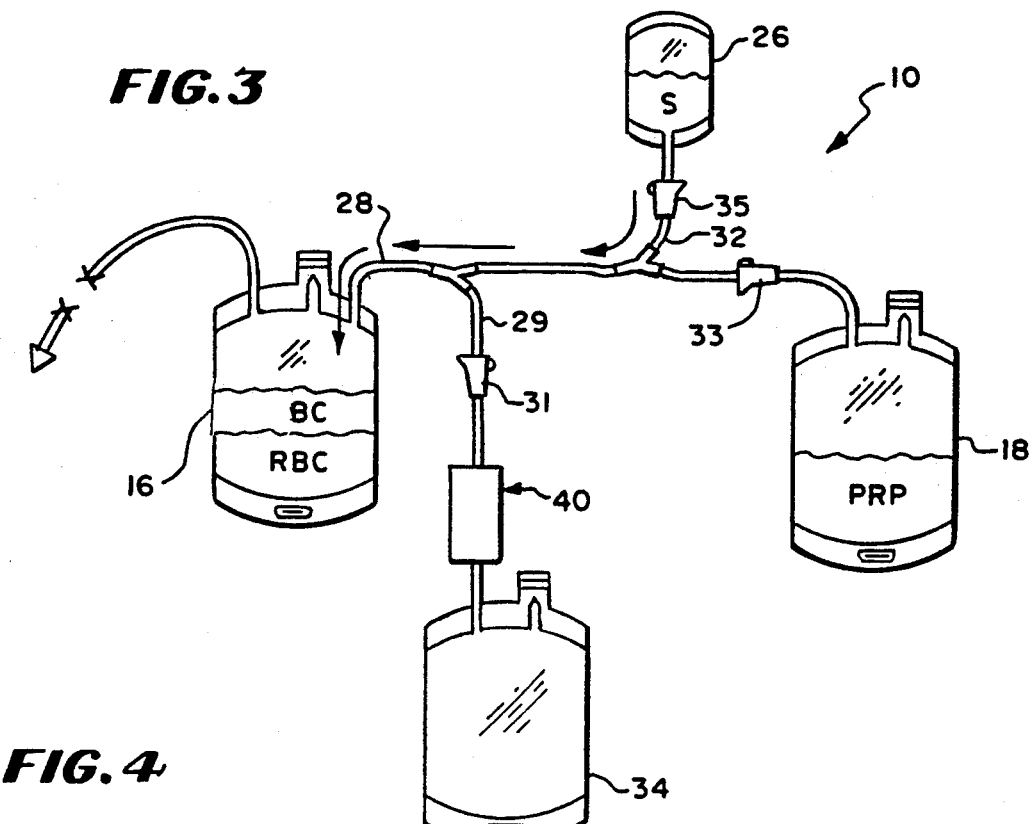
FIG. 3 is a schematic view of the system shown in FIG. 1 being used to transfer an additive solution from the associated transfer assembly into the red blood cells in the primary collection container.

As FIG. 5 shows, the bags 18 and 26 are then themselves separated by forming snap-apart seals "x" in the tubing 30 (as shown in FIG. 3) for subsequent storage of the collected components. The transfer bag 34 (containing the filtered red blood cells) is also separated in the same fashion for storage (as FIG. 5 also shows).

Should air become trapped in the transfer bag 34, it may be necessary to transfer the air through path 28 back into the primary bag 16 before separating the transfer bag 34 from the system 10. As seen in FIG. 9, an air bleed channel 50 can be incorporated within the inline filtration device 40 for this purpose. To prevent flow of the blood cells being filtered through this channel in the filtration step, a suitable one-way valve 52 is provided to close the end of the channel near the inflow opening to filtration device 40. As shown by dotted line 54, an air bleed channel separate from the filter could optionally be provided. Means such as a clamp 55 can be provided to open and close bypass line 54 as required. Clamp 31 is opened during this step to allow the vented air to proceed into the primary bag 16.

A variation in the method of using the system shown in FIG. 1 is shown in FIG. 8. In this alternative method, whole blood is collected and separated in the primary bag 16 in the manner previously described. The same, previously described first processing mode is employed to transfer the platelet-rich plasma component from the primary bag 16 to the transfer bag 18 (as FIG. 2 shows). As before, the transfer of platelet-rich plasma into the first transfer bag 18 leaves the red blood cells and as many white blood cells as possible in the primary bag 16.

In the second processing mode of the alternative method, red blood cell storage solution S is transferred from the transfer bag 26 into the primary bag 16 in the manner previously described (as generally shown in FIG. 3). However, in the alternative method, not all of the additive solution S is transferred during this processing mode. A portion of the additive solution S is left behind in the transfer bag 26 for use later in the process.

In the third processing mode of the alternative method, the mixture of additive solution S and the red blood and white blood cells in the primary bag 16 is transferred into the transfer bag 34 via the separation device 40 in the manner previously described (and as shown by Arrows I in FIG. 8).

In the fourth processing mode of the alternative method, the remainder of the additive solution S present in the transfer bag 26 is next transferred into the transfer bag 34 via the separation device 40 (as shown by Arrows II in FIG. 8). This transfer is accomplished by opening clamps 31 and 35, while closing the clamp 33.

The fourth processing mode of the alternative method serves to flush any red blood cells retained in the separation device 40 free of the device 40 and into the transfer bag 34. Component yields are thereby enhanced to the fullest extent possible.

In a fifth processing mode of the alternative method, constituents of the component contained in the transfer bag 18 are separated and transferred to the bag 26 (now empty of additive solution S) in the manner previously set forth in the fourth processing mode of the first described method (and as shown in FIGS. 4 and 5).

The quantities of additive solution S transferred during the second and fourth processing modes of the alternative method can vary according to the objectives of the procedure. In the illustrated embodiment, where a therapeutic unit of red blood cells is processed, about 75 ml of additive solution S is transferred during the second mode, and about 25 ml more additive solution S is transferred during the fourth mode.

Figure 6:
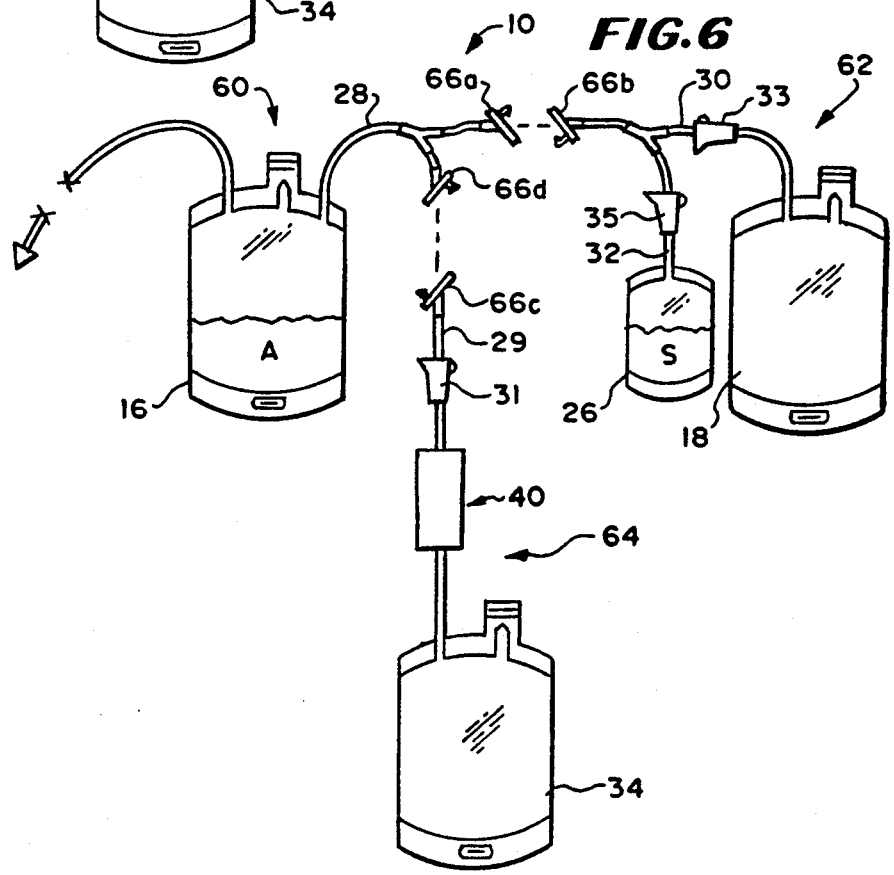
FIG. 6 is a schematic view of an alternative arrangement of the system shown in FIG. 1, in which the various assemblies comprise initially separate subassemblies that are joined together at time of use.

In the embodiment shown in FIG. 6, the system 10 comprises three initially separate subassemblies 60, 62 and 64. The subassembly 60 constitutes a blood collection assembly and includes the primary bag 16 and integrally joined tubing 28. The subassembly 62 constitutes a first transfer assembly and includes the transfer bags 18 and 26 with integrally joined tubing 30 and 32 (with associated roller clamps 33 and 35). The subassembly 64 constitutes a second transfer assembly and includes the transfer bag 34, the inline separation device 40, and the tubing 29 (with associated roller clamp 31).

The separate subassemblies 60, 62, and 64 are joined together at time of use to comprise the system 10 shown in FIG. 1. For this purpose, the embodiment shown in FIG. 6 includes a means for connecting the initially separate subassemblies 60, 62, and 64 together. The connection means is associated with each of the initially separate subassemblies 60, 62, and 64.

In the embodiment shown in FIG. 6, the connection means comprises mating sterile connection devices (designated 66a, 66b, 66c and 66d). The devices 66a, 66b, 66c, and 66d (see also FIG. 7) are described in Granzow et al U.S. Pat. Nos. 4,157,723 and 4,265,280, which are incorporated herein by reference.

The devices 66a and 66d are carried by the tubing 28 of the subassembly 60. The device 66b is carried by the tubing 30 of the transfer subassembly 62. The device 66c is carried by the tubing 29 of the transfer subassembly 64.

All the sterile connection devices (two of which 66a and 66b are shown in FIG. 7 for illustration) each generally includes a housing 70 having a normally closed, meltable wall 72 made of a radiant energy absorbing material. The housings 70 are joined together with mating bayonet-type couplers 74a and 74b, with the walls 72 placed in facing contact. When connected and exposed to radiant energy, the walls 72 melt at temperatures that result in the destruction of bacteria, while at the same time opening a fluid path between the connected housings 70.

The devices 66a, 66b, 66c, and 66d normally close the associated assemblies 60, 62, and 64 from communication with the atmosphere and are opened in conjunction with an active sterilization step which serves to sterilize the regions adjacent to the interconnecting fluid path as the fluid path is being formed. These devices 66a, 66b, 66c, and 66d also hermetically seal the interconnecting fluid path at the time it is formed. The use of these sterile connection devices 66a, 66b, 66c, and 66d assures a probability of non-sterility that exceeds one in a million. The devices 66a, 66b, 66c, and 66d thus serve to connect the subassemblies 60, 62, and 64 without compromising their sterile integrity.

Alternately, the connection means can comprise the sterile connecting system disclosed in Spencer U.S. Pat. No. 4,412,835 (not shown). In this arrangement, this system forms a molten seal between the tubing ends. Once cooled, a sterile weld is formed.

The subassemblies 60, 62, and 64, once sterilized, each constitutes a sterile, "closed" system, as judged by the applicable standards in the United States.

According to the invention, it is possible to direct fluid into and out of the bags 16, 18, 26 and 34 in a desired sequence, with only the red blood cell concentrate passing through the filtration device 40. It will be understood, however, that in the event filtration of any of the other blood components were to be desired, separation devices could be added to the system for such purposes.

In the illustrated embodiments, the entire filtration process can be accomplished in less than five minutes. All blood components processed are substantially free of the undesired matter. In the preferred embodiment, where the all the fluid transfers are made using sterile connection techniques, the processing and inline filtration have occurred without compromising the sterile integrity of any collected component or reducing their storage life.

Various modifications of the invention will be apparent to those skilled in the art within the purview of the following claims.

We claim:

1. A method of collecting blood components comprising the steps of collecting blood having the undesired matter in a blood collection container, separating blood in the blood collection container into a first component and a second component that contains the undesired matter, opening communication between the blood collection container and a first transfer assembly having an empty first transfer container and a second transfer container that contains an additive solution intended for the second component, to (i) convey the first component essentially free of the undesired matter from the blood collection container into the empty first transfer container and (ii) convey the additive solution from the second transfer container into the blood collection container to mix the additive solution with the second component that contains the undesired matter, opening communication between the blood collection container and a second transfer assembly having a third transfer container and a fluid path that leads to the third transfer container and that includes means for separating the undesired matter from the blood, to convey the mixture of the additive solution and the second component that includes the undesired matter into the third transfer container through the separation means to remove the undesired matter, separating the first component within the first transfer container into first and second constituent parts, and transferring the first constituent part into the second transfer container for storage, bypassing the blood collection container, while retaining the second constituent part in the first transfer container for storage.

2. A method according to claim 1 and further including the step, which occurs after the step of conveying the second component into the third transfer container, of expelling air from the third transfer container through a path that bypasses the separation means.

3. A method according to claim 1 and further including the steps of separating the first transfer assembly from the blood collection container, separating the first component within the first transfer container into first and second constituent parts, transferring the first constituent part into the second transfer container, while retaining the second constituent part in the first transfer container, and separating the first transfer container holding the first constituent from the second container holding the second constituent.

4. A method according to claim 1 or 3 and further including the step of separating the third transfer container from the fluid path that includes the separation means.

5. A method according to claim 4 and further including the step of storing the blood components and constituents in their respective transfer containers.

6. A method of collecting blood components comprising the steps of collecting blood having the undesired matter in a blood collection container, separating the blood in the blood collection container into a first component and a second component that contains the undesired matter, opening communication between the blood collection container and a first transfer assembly having an empty first transfer container and a second transfer container that contains an additive solution, to (i) convey the first component from the blood collection container into the empty first transfer container and (ii) convey a first quantity the additive solution from the second transfer container into the blood collection container to mix the additive solution with the second component that contains the undesired matter, opening communication between the blood collection container and a second transfer assembly having a third transfer container and a fluid path that leads to the third transfer container and that includes means for separating the undesired matter from the blood, to convey the mixture of the first quantity of additive solution and the second component that includes the undesired matter into the third transfer container through the separation means to remove the undesired matter, and opening communication between the first and second transfer assemblies to convey a second quantity of the additive solution from the second transfer container through the separation means, bypassing the blood collection container into the mixture contained in the third transfer container and thereby flush additional second component from the separation means.

7. A method according to claim 6 and further including the steps of separating the first component within the first transfer container into first and second constituent parts, and transferring the first constituent part into the second transfer container for storage, while retaining the second constituent part in the first transfer container for storage.

8. A method according to claim 6 and further including the steps of separating the first transfer assembly from the blood collection container, separating the first component within the first transfer container into first and second constituent parts, transferring the first constituent part into the second transfer container, while retaining the second constituent part in the first transfer container, and separating the first transfer container holding the first constituent from the second container holding the second constituent.

9. A method according to claim 6 or 7 or 8 and further including the step of separating the third transfer container from the fluid path that includes the separation means.

10. A method according to claim 10 and further including the step of storing the blood components and constituents in their respective transfer containers.

11. A method according to claim 7 and further including the step, which occurs after the step of conveying the second component into the third transfer container, of expelling air from the third transfer container through a path that bypasses the separation means.

12. A method according to claim 1 or 6 wherein, at the end of the step of separating the blood in the blood collection container, the first component is platelet-rich plasma, the second component is red blood cells, and the undesired matter is white blood cells.

13. A method according to claim 12 and further including the steps of separating the platelet-rich plasma within the first transfer container into platelet-poor plasma and a concentration of platelets, and transferring the platelet-poor plasma into the second transfer container for storage, while retaining the platelet concentration in the first transfer container for storage.

14. A blood collection system comprising, a blood collection assembly, a first transfer assembly comprising an empty first transfer container and a second transfer container that contains an additive solution, a second transfer assembly comprising a third transfer container and a fluid path that leads to the third transfer container and that includes means for separating undesired matter from blood, and means for directing fluid flow within the system including flow control means operable (i) in a first mode for directing a first quantity of blood from the blood collection assembly for collection in the first transfer container, (ii) in a second mode for directing additive solution from the second transfer container into the blood collection assembly to mix with the quantity of blood remaining in the blood collection assembly, (iii) in a third mode for directing the mixture of the additive solution and the remaining blood from the blood collection assembly to the third transfer container through the separation means to remove the undesired materials, and (iv) in a fourth mode for directing a constituent of the blood contained in the first transfer container into the second transfer container bypassing the blood collection assembly for collection.

15. A system according to claim 14 wherein the second transfer assembly includes means for venting air from the third transfer container in a path that bypasses the separation means.

16. A blood collection system comprising, a blood collection assembly, a first transfer assembly comprising an empty first transfer container and a second transfer container that contains an additive solution, a second transfer assembly comprising a third transfer container and a fluid path that leads to the third transfer container and that includes means for separating undesired matter from blood, and means for directing fluid flow within the system including flow control means operable (i) in a first mode for directing a first quantity of blood from the blood collection assembly for collection in the first transfer container, (ii) in a second mode for directing a first quantity of the additive solution from the second transfer container into the blood collection assembly to mix with the quantity of blood remaining in the blood collection assembly, (iii) in a third mode for directing the mixture of the additive solution and the remaining blood from the blood collection assembly to the third transfer container through the separation means to remove the undesired materials, (iv) in a fourth mode for directing a second quantity of the additive solution from the second transfer container into the third transfer container through the separation means, bypassing the blood collection assembly, and (iv) in a fifth mode for directing a constituent of the blood contained in the first transfer container into the second transfer container for collection.

17. A system according to claim 16 wherein the second transfer assembly includes means for venting air from the third transfer container in a path that bypasses the separation means.

18. A system according to claim 14 or 16 wherein at least one of the blood collection assembly, the first transfer assembly, and the second transfer assembly comprises an initially separate subassembly, and further including means for attaching the separate subassembly to the other parts of the system.

19. An assembly usable in association with a primary blood collection system, the assembly comprising a first transfer container made of a material that, when compared to DEHP-plasticized polyvinyl chloride materials, has a greater gas permeability that is beneficial for platelet storage, a second transfer container that holds an additive solution for red blood cells, conduit means having one branch that communicates with the first transfer container, a second branch that communicates with the second transfer container, and a third branch that joins the first and second branches and includes means for connecting the conduit means and associated containers to a primary blood collection system, and means operative, when the conduit means is attached to the primary blood collection system, for directing fluid flow between the conduit means and the blood collection system and including flow control means operative (i) in a first mode for directing a platelet-rich blood component from the primary collection system into the first transfer container;

(ii) in a second mode for directing the additive solution from the second transfer container to the primary blood collection system; and (iii) in a third mode for directing a platelet-poor constituent separated from the component contained in the first transfer container into the second transfer container, leaving a concentration of platelets in the first transfer container for storage.

* * * * *

UNITED STATES PATENT AND TRADEMARK OFFICE
CERTIFICATE OF CORRECTION

PATENT NO. : 5,269,946

DATED : December 14, 1993

INVENTOR(S) : Goldhaber et al.

It is certified that error appears in the above-identified patent and that said Letters Patent is hereby corrected as shown below:

On the title page, item
On the face of the patent
    At [75] Inventors, add "Kenneth M. Johnson, Lindenhurst, Illinois"
    At [73] Assignee, change "Deerfield, Mich." to read --- Deerfield, IL ---

Column 9, Line 13  After "component" insert --- essentially free of the undesired matter ---
Column 9, Line 20  After "component delete "essentially free of the undesired matter ---
Column 10, Line 63  After "claim" delete "10" and substitute --- 9 ---
Column 10, Line 66  After "claim" delete "7" and substitute --- 6 ---
Column 12, Line 19  Delete (iv) and substitute --- (v) ---

Signed and Sealed this

Fifth Day of May, 1998

*Attest:*

BRUCE LEHMAN

*Attesting Officer*    *Commissioner of Patents and Trademarks*